United States Patent [19]
Dullien

[11] Patent Number: 5,370,135
[45] Date of Patent: Dec. 6, 1994

[54] USE OF ESTRIOL MEASUREMENT TO MONITOR TOCOLYTIC THERAPY

[75] Inventor: Vivian K. Dullien, Boulder, Colo.

[73] Assignee: Biex, Inc., Boulder, Colo.

[21] Appl. No.: 136,219

[22] Filed: Oct. 13, 1993

[51] Int. Cl.$^5$ ............................................. A61B 19/00
[52] U.S. Cl. ................................................. 128/89.8
[58] Field of Search ............................... 128/897–899; 600/33–35; 436/65

[56] References Cited

U.S. PATENT DOCUMENTS 4,500,523 2/1985 Nathanielsz ..................... 514/178

OTHER PUBLICATIONS

Anderson and Turnbull, Am. J. Obstet & Gynecol, Dec. 15, 1969, 105:8:1207–1214.
Turnbull et al., The Lancet, Sep. 23, 1967, 102:627–629.
Turnbull et al., The Lancet, Jan. 26, 1974, pp. 101–104.
Turnbull, European J. of Obstet & Gynecol and Reproductive Biology, 1989, 33:11–24.
Higby et al., Am. J. Obstet & Gynecol, Apr. 1993, 168:1247–59.

*Primary Examiner*—William E. Kamm
*Assistant Examiner*—John P. Lacyk
*Attorney, Agent, or Firm*—Cooley Godward Castro Huddleson & Tatum

[57] ABSTRACT

A method of monitoring tocolytic therapy, which comprises determining a first concentration of estriol in a body fluid of a pregnant patient undergoing or diagnosed as a candidate for undergoing treatment with a tocolytic agent and, based on the value of the first concentration relative to a standard, either initiating, continuing, discontinuing, or modifying the treatment.

13 Claims, No Drawings

USE OF ESTRIOL MEASUREMENT TO MONITOR TOCOLYTIC THERAPY

INTRODUCTION

1. Technical Field

This invention relates to techniques for determining when tocolytic therapy should be initiated and to what extent and duration it should continue.

2. Background

Premature birth is the leading cause of infant morbidity and death in the United States and other developed countries. When a patient goes into pre-term labor, an attending physician has the option of allowing the delivery to proceed or attempting to stop uterine contractions with tocolytic agents. While many factors will affect this decision, a primary factor is the gestational age of the fetus. Tocolytic agents are generally used between 24 and 32 weeks of gestation, as the goal of therapy ideally is to prolong gestation to or beyond 32 weeks. However, a delay of even one week during this time can be significant, because of the rapid development of the fetus and the greatly improved chances for survival with each additional week of prolonged gestation.

A number of different tocolytic agents have been used for treating premature labor. However, it has been difficult in the past to determine when therapy should properly begin or to decide when it should be decreased, increased, or halted. Some studies have indicated that the diagnosis of pre-term labor may be in error as much as 80% of the time (M. O'Driscol, Discussion in: Anderson et al., eds., Pre-Term Labour, Proceedings of the Fifth Study Group of the Royal College of Obstetricians and Gynaecologists London, Royal College of Obstetricians and Gynaecologists 1977: 369-70). Excessive uterine contractibility and cervical dilation have been used in the past and are currently used to diagnose impending premature labor; fetal breathing movements have been investigated. See Turnball, *Eur, J. Obstetrics & Gynecology and Repro. Biol.* 33:11-24 (1989); Anderson, *Am. J. Obstetrics & Gynecology* 105:1207-14 (1969). In about 30% of apparent pre-term labor cases, uterine contractions cease spontaneously without treatment (M. Wynn and A. Wynn, The Prevention of Pre-term Birth, London, Foundation for Education and Research and Child Bearing, 1977). Although labor is often diagnosed by the presence of regular uterine contractions combined with cervical dilation and effacement, many investigations have based the diagnosis of pre-term labor on contractions alone (K. Higby, et. al., Do Tocolyac Agents Stop Pre-term Labor? A Critical and Comprehensive Review of Efficacy and Safety, *Am. J. Obstet. Gynecol., April* 1993, 1247-1259). The error in diagnosis with contractions used as a sole diagnosis criteria is estimated to be from about 40 to about 70% (S. N. Caritis, et. al., Pharmacologic Inhibition of Pre-term Labor, *Am. J. Obstet. Gynecol.,* 1979, 133:557-578).

Tocolytic agents are administered in order to reduce or prevent uterine contractions once pre-term labor has been diagnosed. However, tocolytic agents can have adverse side-effects, so care must be taken in determining whether therapy should begin or continue. In addition, evaluation of when tocolytic therapy should be stopped is also somewhat confused. Criteria utilized include simple temporary arrest of uterine contractions, no further change in cervical dilation or effacement, as well as combinations of these clinical symptoms. However, in many cases an initial arrest of uterine contractions will be followed by additional contractions once therapy is halted. At the present time there are no clinical assays for determining the extent or duration of tocolytic therapy designed to prevent uterine contractions and thus premature birth.

Accordingly, a clinical assay to provide additional useful information to a physician who must decide whether to initiate, continue, decrease, increase, or halt tocolytic therapy would be useful.

Previous investigations by the present inventor have indicated that estriol levels are predictive of premature onset of labor. See U.S. patent application Ser. No. 07/952,438, filed Sep. 28, 1992. However, the value of estriol level measurement during labor to monitor the effectiveness of tocolytic agents has not previously been reported.

SUMMARY OF THE INVENTION

Accordingly, it is an object of this invention to provide a simple biochemical assay that will allow an attending physician to monitor the correct beginning time for and duration of tocolytic therapy.

It is a further object to provide a quantitative assay for efficacy of tocolytic treatment so that continued tocolytic treatment can be adjusted to the minimum effective pharmaceutical level.

These and other objects of the invention as will hereinafter become more readily apparent have been accomplished by providing a method of monitoring tocolytic therapy, which comprises measuring a first concentration of estriol in a body fluid of a pregnant patient undergoing or diagnosed as a candidate for undergoing treatment with a tocolytic agent; correlating the concentration with a pre-determined standard estriol concentration; and either initiating, continuing, discontinuing, or modifying the tocolytic treatment in response to the relative values of the first estriol concentration and the standard estriol concentration.

DESCRIPTION OF SPECIFIC EMBODIMENTS

The present invention provides a method for monitoring the efficacy of tocolytic treatments that reduce or eliminate uterine contraction in order to delay the onset of labor, especially pre-term labor, in a pregnant human. It has now been found that monitoring estriol concentrations in a body fluid before or during treatment with a tocolytic agent allows a physician to reach better decisions on whether to begin or continue the tocolytic treatment or whether the treatment should be discontinued or modified.

This method is quantitative and allows a physician to adjust the nature of the treatment as well as to determine when it should begin or end. In summary, the method involves measuring a first concentration of estriol in a body fluid of a pregnant patient undergoing, or diagnosed as a candidate for undergoing, treatment with a tocolytic agent. This first concentration is compared to a standard, and various actions are taken depending on the relative value of the measured concentration and the standard, as well as on the history of the patient prior to the measurement in question. In general, a measured estriol concentration above the standard value is an indication that tocolytic treatment should be initiated or, if already initiated, should be continued or increased in intensity. In a similar manner, if the estriol concentration is below the standard value, tocolytic treatment will not be initiated or, if already initiated, will be decreased or halted depending on the measured concentration relative to the standard. Because estriol measurement is straight-forward and can be carried out at the bedside, an attending physician can obtain quantitative results very rapidly, which is of great assistance in reaching a clinical decision.

For example, the assay can be carried out on a single saliva sample using a simple diagnostic kit with an enzyme label. Similar commercial assays for other substances are now available, and a laboratory assay for estriol using radioactive labels is already available commercially. In this invention, there are no limitations on the type of assay used to measure estriol. Any of the current assays for estriol can be used, as well as assays that may be developed in the future. Examples of estriol assays are described in detail below.

The assay can be carried out on any body fluid, such as blood (or a blood fraction, especially serum or plasma), urine, cervical or vaginal secretions, sweat, or saliva. The assay is usually carried out on a sample but can be monitored in vivo if desired. Estriol is sufficiently soluble in water so that it is distributed in fluids throughout the body. Saliva is preferred for simplicity of sampling and because, unlike in urine, detection is not complicated by the presence of estrogen conjugates.

For ex vivo monitoring, a "sample" is the material being analyzed and is usually of direct biological origin, although pre-treatment may have removed some of the normal biological compounds normally associate with the analyte (such as red cells separated from plasma in a whole blood sample). Assays are preferably directed to detection to free estriol, since conjugated estriol has reduced biological activity. In saliva about 92% of estriol is in the free form, while most estriol in urine is present as a conjugate. As will be clear to those familiar with steroid metabolism, an estriol conjugate is a compound formed by formation of a covalent linkage of a non-steroidal compound to estriol. Linkage is typically through a hydroxyl group of the steroidal ring system. The non-steroidal component can be inorganic (e.g., a sulfate group) or organic (e.g., a glucuronide group).

In the broader aspects of the invention, them are no limitations on the collection and handling of samples as long as consistency is maintained. With some body fluids, such as saliva and plasma, them is little diurnal variation in estriol levels. For other fluids, notably urine, variations occur, and it is preferred to eliminate variations to the extent possible, for example by taking samples at the same time of day. However, other techniques can be utilized to ensure consistency of measurement of analytes in clinical fluids. For example, creatinine can be measured concurrently with estriol in urine. Creatinine is produced at a constant rate in the kidneys, and measurement of creatinine concentration allows correction of volume errors in urine samples, as is well known in the art. However, urine is not a preferred sample since the sample will normally be taken under conditions of imminent or concurrent uterine contractions. Accordingly, saliva is a particular preferred body fluid because of the ease with which it can be obtained.

If desired (but not required in the broadest applications of this invention), and depending on the source of the fluid being tested, free estriol can be separated from estriol conjugates. Techniques for such separations are known in the art. See, for example, Evan, *N. Z. Med. Lab. Tech,* 33:86 (1979), which describes such separations as well as two radioimmunoassays useful for measuring plasma estriol. However, these separations are generally difficult, and assays that do not require separation, either because of the use of specific antibodies or other binding compounds that differentiate between free and conjugated estriol, or because the sample is obtained from a source containing mostly free estriol, such as saliva, are preferred.

The concentration of estriol in the fluid assayed is correlated with a standard value to determine when to initiate, increase, decrease, cease, or otherwise modify the tocolytic treatment. The standard is usually (1) a predetermined range of estriol concentrations for the same body fluid in normal pregnant humans in the general population, either at the corresponding time in the pregnancy or a specific time relative to normal termination of pregnancy, or (2) a previously measured estriol concentration of the same body fluid of the same pregnant human. A measured higher concentration of estriol relative to the standard value is an indication of potential onset of pre-term labor and therefore an indication that tocolytic treatment should be initiated or, if already initiated, should be increased in intensity. The method of the invention does not require the measurement of any other substance, such as the progesterone concentration in the body fluid, or require the measurement of total estriol production over a time interval. However, measurements of total estriol over a given time period, such as 24 hours, can be used with urine, if desired, and other substances important to fetal or maternal well being, such as progesterone, can be concurrently measured if desired.

Prior to the investigations in the laboratory of the present inventor reported in the Background section of this specification, there was no predictive test for pre-term labor. Likewise, before the method of the present invention, there was no technique for monitoring tocolytic treatment. Accordingly, it is difficult to predict the variations of treatment that may arise among physicians and other care providers now that the various diagnostic tests based on estriol concentration have been developed. A single elevated sample in a high risk patient at an early gestational age would probably be adequate for most physicians to initiate tocolytic therapy. However, other physicians may choose to wait for other clinical criteria such as uterine contractions and cervical change, and/or for a recurrence of an elevated estriol level.

A single salivary estriol sample can determine impending or potential pre-term labor, as described herein; however, the attending physician will most likely determine when to begin tocolytics by considering the estriol level among other factors, such as the physical condition, size and weight of the patient, the severity of uterine contractions, and the extent of cervical dilation.

The first general standard set out above, namely a predetermined range of estriol concentrations for the same body fluid in normal pregnant humans in general, is typically obtained by using the same assay technique that will be used in the application of the method to an individual being tested, in order to ensure the highest correlation. Sufficient measurements are made in a normal population of pregnant women to produce a statistically significant range of normal values for the value to which a comparison will be made, which typically is at preselected time intervals during normal pregnancy. While comparison to a time immediately prior to normal delivery (38 to 40 weeks) is often used, other time periods can be used. For example, estriol levels during a given week of an individual pregnancy (i.e., that of the subject patient) can be compared to the normal range of concentrations for the same time period (e.g., the 20th week). Generally, the minimum concentration indicative of possible onset of labor and thus continued or initial tocolytic intervention is considered to be at least 1, preferably at least 2, more preferably at least 3, and most preferably at least 4, standard deviations above the mean estriol concentration determined for any given body fluid just prior to the onset of labor for normal pregnant humans.

It will be recognized by those familiar with statistics that the number of standard deviations used as a standard value for monitoring tocolytic treatments will be selected with an appropriate treatment goal in mind. For example, one standard deviation would encompass about 68% of normal samples; that is, 32% of normal samples would be expected to fall outside the lower and upper limits set by one standard deviation from the mean (16% would thus be expected to be above the selection limit). Thus, one standard deviation above the normal mean is not used for routine initiation of tocolytic treatment, as it would include too many false positives. However, one standard deviation below the mean is appropriate for an indication that tocolytic treatment should be decreased or halted, particularly if present in association with other appropriate clinical signs, as discussed in the Background section above. Two standard deviations from the mean would encompass about 95% of normal samples; three standard deviations, about 99%; four standard deviations, more than 99%. These levels are more appropriate generally for initiation of tocolytic treatment, especially for patients whose levels of estriol are known to be normal or slightly above normal or to vary from sample to sample as well as for assays with a high coefficient of variance.

It is not necessary to express the lower limit for the continuation or initiation of tocolytic treatment (upper limit of the normal range) in standard deviations. Any other system that can be used to provide a statistically significant indication of probable onset of labor can be used. For example, the limit can be set to be a concentration that is at least as high as the 95th percentile concentration for normal patients for the same body fluid for a normal pregnancy. In any case, it is preferred to select a normal level from the 38–42 week period for normal pregnancies, preferably at 40 weeks, and to monitor the concentration at 30 weeks or earlier.

Because of the many different possible clinical goals, the actual estriol level indicative of initiation of tocolytic treatment to avoid pre-term labor is best selected by the attending physician after collecting data from several samples during the initial portion of the pregnancy and taking into consideration the time at which the measurement is being made. For example, in a normal pregnancy at week 30, the change expected in the estriol concentration prior to the onset of labor is smaller than 2 standard deviations from the mean concentration of estriol at 30 weeks. Thus, while assays in the first portion of a pregnancy (prior to 30 weeks) might use 3 or 4 standard deviations as an indication of onset of labor, two, one and a half, or even one standard deviation would be more appropriate in the later portion of a pregnancy (e.g., after 30 weeks) depending on the condition of the patient, other clinical indications in the mother known to the attending physician, and the health of the fetus. Of course, it is the earlier stages of a pregnancy that require greater attention to avoiding pre-term labor, because of the lack of fetal development at these stages and the high risk of infant death post partum. Pre-term labor is thus preferably considered to be any labor prior to end of a normal 39-week term of pregnancy. The method of the invention is preferably used for pregnancies during weeks 20 to 36, when prolonging pregnancy for even a short time is most efficacious in reducing the effects of premature birth. However, the assay, particularly when used to detect rate of increase, is still applicable for pregnancies terminated by labor and delivery after the end of 40 weeks, and measurements made during this time period are also considered to fall within the scope of the invention. When applied to weeks 38 and higher, the invention is normally practiced using the "self-comparison" method discussed in more detail below; i.e., by comparing the measurement at a given time with a measurement made earlier with the same patient.

In a similar manner, subject to the same constraints discussed above, an assay concentration at least 1, preferably at least 2, more preferably at least 3, and most preferably at least 4, standard deviations above the mean normal concentration for the same stage of pregnancy can also be used as an indication of potential onset of labor, and thus an appropriate time for administration of a tocolytic agent, although the probability is lower if the measured level does not reach the levels considered normal for weeks 38–42.

Standard values will vary with the specific body fluid whose concentration is being measured and with the specific assay being used (although to a lesser extent). Typical minimum indicative levels of labor onset (and thus initiation of tocolytic treatment) in an assay that measures unconjugated estriol are as follows for the indicated body fluids (all concentrations are in nM): saliva, at least 3, preferably at least 5, more preferably at least 7; serum, 30, preferably at least 35, more preferably at least 45.

As an alternative to comparing estriol concentrations to those present in a normal population, a previously measured estriol concentration of the same body fluid of the same pregnant human can be used as a standard for comparison. In this case, what is being determined is usually the rate of increase in estriol concentration in the fluid being tested. A positive indication of initiation of tocolytic treatment (i.e., indication of imminent onset of labor) is considered to be present when the measured concentration exceeds a previously measured estriol concentration made in the same body fluid in the same pregnant human female by 50%, preferably 75%, more preferably 100%, within one week. Again the selection of a particular rate of increase to label as the lower limit of labor onset is best selected by the attending physician for the particular reason desired. For example a screening test that is intended to collect potential problem patients into the hospital for further observation and study could select the 50% increase as its limit in order to avoid false negative results, while accepting the problems caused by including a relatively large number of false positives. Higher percentage increases as the minimum positive indication are more acceptable for assays in which the physician is present and is able to interpret other clinical signs, in the same manner as described above for standard deviations from the normal population mean. Increases in estriol concentration that meet the standards of this paragraph and additionally reach levels previously indicated to be indicative of the onset of labor in normal populations of patients are particularly likely to indicate imminent onset of labor.

Most of the discussion above addresses the issue of initiation of tocolytic treatment. However, since increased estriol concentrations above normal values continue to be an indication of likely re-initiation of pre-mature labor even after an initial tocolytic treatment, continuing to monitor estriol concentrations allows a physician better control over further tocolytic treatment. At the beginning of tocolytic treatment, estriol concentrations can preferably be monitored at daily intervals for at least one week, then at weekly intervals, depending upon results. For example, if estriol measurements are continued during treatment and a decrease is seen to normal estriol levels, tocolytic treatment can be halted. On the other hand, if uterine contractions cease after tocolytic treatment but the estriol levels remain high, then there is a high probability that labor will begin again if tocolytic treatments are halted. Accordingly, tocolytic treatments should be continued, if appropriate when considered in combination with other clinical symptoms. Furthermore the intensity of the tocolytic treatment (see below for specific treatments) can be either increased or decreased depending on the value of the estriol concentration relative to the standard value. If the measured value is significantly higher than the standard and shows no sign of decreasing, then the intensity of the tocolytic treatments can be increased. Conversely, if the estriol levels remain higher than normal, but have been reduced somewhat by the initial tocolytic treatment, then either the initial treatment can be continued at its initial intensity or the intensity of the treatment can be reduced, with continuous monitoring of the effect of the treatment of estriol concentration.

The situation regarding continued tocolytic treatment as indicated by the estriol level is somewhat more complicated than the initial initiation of tocolytic treatment. While a physician may halt tocolytic treatment when the estriol concentration drops below the standard chosen as an indication of initial treatment, such patients should be carefully monitored as they are predisposed to re-initiation of pre-term labor. It may be more desirable, depending on the specific clinical symptoms that accompany the tocolytic treatment, to continue tocolytic treatment until the measured value reaches the mean standard value or even some value below the mean to provide better control of labor re-initiation.

It will be recognized by those skilled in clinical analysis that assays for a given analyte, including this assay for estriol, and the resulting modification of treatment, such as this tocolytic treatment, are not expected to be obtained or to be interpreted by an attending physician in the absence of additional information. Additionally, the results of any assay are best considered to be indicative of the probability of the presence of a clinical condition rather than as absolute proof. The same situation exists for the present invention. Nevertheless, an indication of increased probability of onset of labor is clinically useful information and can be used by a skilled medical practitioner in combination with other information to care for patients in a more informed manner than would be possible if the information were not available.

A quantitative enzyme immunoassay or radioimmunoassay for laboratory testing may be utilized with the present invention. Alternatively, a preferred assay for use with the present invention is described in U.S. application Ser. No. 07/857,606, filed Apr. 1, 1992, which is herein incorporated by reference. This assay utilizes an enzyme-labelled component (here a labelled estriol molecule or derivative thereof) in a competitive binding assay for estriol. The assay is a non-instrumented enzyme immunoassay that provides present/not-present or "threshold" (+/−) analysis results at a preselected cut-off value and thus is well adapted for home and office use with the present invention.

In a typical assay using this technique, the enzyme-labelled, competitive binding component comprises estriol (or the portion thereof used to generate the antibody used in the assay) bound to the immunogen that is used to produce the antibody of the assay. An enzyme label is bound to this moiety, preferably through a bulky linker such as an avidin-biotin complex. The use of such a competitive binding compound allows antibodies to be used without attempting to manipulate affinity of binding of antibody to competitor while still providing the steep competitive binding curve required for a +/− analysis.

In a typical assay, antibody is attached to a solid surface, such as a microliter plate well, a test tube, or a porous reagent strip (such as cellulose or glass fibers). The antibody-coated solid surface is then contacted simultaneously with a sample and with a competitive binding compound. By providing fewer antibody binding sites than are present in the combined total of analyte and competitive binding compound, only a fraction of the molecules in solution will bind to the solid surface. If there are no analyte molecules present, all of the binding sites will be taken up by the competitive binding compounds so that a maximum amount of enzyme is attached to the solid surface. When a substrate for the enzyme is contacted with the solid surface after the sample is washed away, reaction of the enzyme with the substrate provides a detectable signal (usually formation of a color) that indicates to the user the absence of analyte in the sample (a negative result). If analyte is present in the sample, analyte competes for binding sites so that less of the enzyme-labelled competitor can bind. By using a bulky binding composition, which binds less rapidly to the antibody than does the analyte, and by properly selecting the number of binding sites relative to the amount of sample added (which is a standard technique to one of skill in the an), analyte present at a concentration above a preselected minimum level will exclude binding of the competitive binding composition and thus binding of the enzyme to the solid substrate. An example of such a selection process to provide different threshold levels is set out in the cited patent application for estradiol. The same selection process can be used with estriol to carry out an assay of the invention. Thus, if sufficient analyte is present in the sample, after reaction no enzyme is present to produce a color change and the reaction mixture stays the same (thus a positive reaction using this reaction scheme).

Other reaction schemes can be used in which the formation of color is indicative of the presence of the analyte. The previous example is merely one of many types of competitive binding assays in which estriol can be measured.

Antibody production for use in an assay for estriol is conventional and is not described here in detail. Techniques for producing antibodies are well known in the literature and are exemplified by the publication *Antibodies: A Laboratory Manual* (1988) eds. Harlow and Lane, Cold Spring Harbor Laboratories Press, and U.S.

Pat. Nos. 4,381,292, 4,451,570, and 4,618,577. For an example of production of antibodies specific for estradiol, see Lasley et al., Fertility and Sterility (1985) 43:861–867, and Munro et al., Abstract, Society for Gynecologic Investigation, San Diego, March 1989. The same techniques can be used to produce antibodies to estriol. A brief discussion of general techniques for the production of antibodies specific for steroids is included for those who may be unfamiliar with the process.

An animal is injected with a composition containing estriol covalently attached to an immunogen, usually a protein, prepared as described above. Multiple injections or the use of an adjuvant will ensure maximum stimulation of the immune system and production of antibodies. If polyclonal antibodies are desired, they can be prepared by simply collecting blood from the immunized animal and separating the antibodies from other blood components by standard techniques. To obtain monoclonal antibodies, the spleen or lymphocytes from the immunized animal are removed and immortalized or used to prepare hybridomas by cell-fusion methods known to those skilled in the art. Antibodies secreted by the immortalized cells are screened to determine the clones that secrete antibodies of the desired specificity. For monoclonal anti-estriol antibodies, the antibodies must bind to estriol. Cells producing antibodies of the desired specificity are selected, cloned, and grown to produce the desired monoclonal antibodies.

Antibody can be attached to a solid surface for use in an assay of the invention using known techniques for attaching protein material to solid support materials. The solid support can include plastic surfaces of test tubes or microtiter plates, polymeric beads, dip sticks, or filter materials. The attachment methods include non-specific adsorption of the protein to the support and covalent attachment of the protein, typically through a free amino group, to a chemically reactive group on the solid support, such as an activated carboxyl, hydroxyl, or aldehyde group.

Specific Tocolytic Treatments

The invention can be carried out with any tocolytic treatment, since it now appears that all such treatments are associated with modifications in the estriol level in the body fluids of the mother. A number of different classes of drugs that inhibit uterine concentration have been suggested and are discussed below by drug class. However, the invention is not limited to the named tocolytic treatments, either individually or by class.

β-Adrenergic Agonists

Isoxsuprine was the first β-sympathomimetic agent used to treat premature labor, in 1961. Since then the functionally related compounds orciprenaline, metaproterenol, salbutamol, albuterol, nylidrin, terbutaline, ritodrine, hexoprenaline, and fenoterol have been used.

Like the endogenous catecholamines epinephrine and norepinephrine, these drugs stimulate β-adrenergic receptors in the uterus and other organs. There are two types of β-adrenergic receptors in humans. $\beta_1$-Adrenergic receptors predominate in the heart, small intestine, and adipose tissue; $\beta_2$-adrenergic receptors are found in smooth muscle of the uterus, blood vessels, diaphragm, and bronchioles. β-Adrenergic agonists affect smooth muscle cells through membrane-mediated binding to β-adrenergic receptors that activates adenylate cyclase. This leads to an increase in intracellular cyclic adenosine monophosphate, which, in turn, initiates a series of reactions resulting in reduced intracellular levels of calcium and reduced sensitivity of the myosin-actin contractile unit to available calcium. The inhibitory effect on the uterus occurs even in the presence of oxytocin. Continued exposure to β-adrenergic agonists leads to desensitization. With prolonged exposure, the number of β-adrenergic receptors decreases (down-regulation), further reducing the effect of the drug.

β-Adrenergic agents cause many unwanted effects because β-adrenergic receptors are present in multiple organ systems. The cardiovascular system is most often involved. However, effects are also seen on the pancreas, kidney, gastrointestinal tract, and liver. The most frequently observed maternal symptoms are nausea, vomiting, tremor, and palpitations. Women also experience headache, thirst, restlessness, and chest pain.

The most common effects on the cardiovascular system are increases in heart rate, systolic blood pressure, pulse pressure, stroke volume, and cardiac output. There is a concomitant decrease in diastolic pressure and peripheral vascular resistance. Cardiac output can increase up to 60% over baseline levels. Mean arterial pressure does not change significantly. Cardiac arrhythmias have been reported. The most common is supraventricular tachycardia; the arrhythmias include atrial fibrillation, premature atrial contractions, and ventricular ectopy.

Increased heart rate and myocardial contractility can predispose to myocardial ischemia. Coronary artery perfusion is decreased as a secondary result of a decrease in diastolic blood pressure and diastolic filling time. These effects can cause micronecrosis of the myocardium. The electrocardiogram changes most frequently observed are transient ST segment depression and inverted T waves. These changes, which may be present in up to 76% of women treated with ritodrine, are often not associate with symptoms. They may be caused by relative hypo-perfusion of the subendocardium. Others, who found no changes in cardiac enzyme levels, concluded that the electrocardiogram findings do not indicate significant myocardial damage. The electrocardiogram findings, which usually resolve with discontinuation of therapy, may not be due to myocardial ischemia, but rather to electrolyte imbalances.

Pulmonary edema occurs in up to 5% of patients treated with β-sympathomimetics. Pulmonary edema occurs with and without concurrent glucocorticoid therapy. Many cases are secondary effects of fluid overload resulting from the antidiuretic effect of high does of β-sympathomimetics. Fluid overload can also be a secondary result of excessive administration of intravenous fluids.

Plasma renin and arginine vasopressin are increased during infusion of β-adrenergic agonists. This increase is associated with sodium and water retention, which predisposes to pulmonary edema. Pulmonary edema is more common in twin gestations. Infection may also play a role in the development of this complication. In the absence of underlying disease, most cases of pulmonary edema can be attributed to intravenous fluids and to ignoring signs of fluid overload.

β-Sympathomimetics increase maternal blood glucose about 40% with a concurrent increase in insulin secretion. The rise in glucose levels is even more pronounced in diabetes, probably because stimulation of glucagon secretion results in gluconeogenesis and glycogenolysis. Insulin levels rise as a result of hyperglycemia and also from direct stimulation of β-adrenergic receptors in the maternal pancreas. Insulin release precedes the onset of hyperglycemia. The effect is heightened by concomitant administration of corticosteroids. β-Adrenergic agonists also include lipolysis, which increases acidic metabolites and can lead to severe metabolic acidosis in diabetic patients.

Serum potassium concentrations decrease rapidly at initiation of treatment with β-sympathomimetics. The potassium concentration is usually 0.6 to 1.5 mEq below pretreatment levels. This decrease in serum levels is probably due to a net flux of potassium from the extracellular to the intracellular space. The hypokalemia is transient; replacement therapy is not indicated. Levels normalize within 24 hours of initiation of tocolysis.

Other effects reported include maternal transaminase elevations, paralytic ileus, myotonic muscular dystrophy, postpartum cardiomyopathy, respiratory arrest caused by muscle weakness in a patient with myasthenia gravis, acute cutaneous vasculitis, allergic dermatitis, hypertensive crisis, cardiac failure, agranulocytosis, cerebral ischemia, second-degree hear block, massive vulvar edema, adult respiratory distress syndrome, severe hemolytic anemia, and maternal death.

β-Sympathomimetics rapidly cross the placenta. Stimulation of β-adrenergic receptors in the fetus probably evokes the same responses as in the mother. Cardiovascular effects include fetal tachycardia, increased cardiac output and redistribution of fetal blood flow, increased thickness of the fetal ventricular septum, neonatal supraventricular tachycardia, myocardial ischemia, myocardial necrosis, hydrops, and hypoglycemia and hyperinsulinemia in the neonate.

Studies examining alterations in uteroplacental blood flow have been conflicting. Some report decreased blood flow, others increased uteroplacental blood flow, and still others no significant change. Alterations in blood flow are not associated with significant changes in fetal hemodynamics. The differences may be attributed to the duration of infusion, the drug used, concurrent use of other medications, and the method used to measure uteroplacental blood flow.

Magnesium Sulfate

Magnesium inhibits myometrial activity in vitro and in vivo. Magnesium inhibits uterine contractions induced by calcium and transiently inhibits further calcium response.

The mechanism by which magnesium sulfate exerts its tocolytic effect is unknown. Presumably, myometrial contractility is depressed by modulating calcium uptake, binding, and distribution in smooth muscle cells, take, binding, and distribution in smooth muscle cells. In high concentrations magnesium blocks calcium influx by competing for calcium binding sites on the cellular membrane. Magnesium activates adenylate cyclase and increases cyclic adenosine monophosphate, thus reducing intracellular calcium. Serum concentrations of 4 to 8 mEq/L appear to be necessary for reduction of myometrial activity.

Dual-agent tocolysis after failure of single-agent therapy has also been reported in the scientific literature. Twenty-three patients were treated with a combination of magnesium sulfate and ritodrine or terbutaline. Delivery was delayed for ≧48 hours or more in 60.9% of patients, but pulmonary edema developed in 22% of the patients.

When magnesium sulfate therapy is maintained in the nontoxic range, maternal side effects are few. Nausea, vomiting, ileus, visual blurring, diplopia, headaches, weakness, lethargy, shortness of breath, pulmonary edema, alterations in calcium metabolism, and urinary retention have been reported. Hypermagnesemia can occur in the presence of impaired renal function. Excessive levels of serum magnesium have been associated with respiratory depression, subendocardial ischemia, cardia arrest and death.

Magnesium sulfate crosses the placenta. Fetal plasma concentrations are comparable to those in the mother. Neonatal hypotonia and drowsiness have been reported. Bony abnormalities and congenital rickets in the newborn have been associated with magnesium sulfate infusion for tocolysis.

Oxytocin Antagonists

Labor, term or pre-term, is associated with an increase in myometrial oxytocin receptors. Myometrial oxytocin receptors increase twelve-fold at term, compared with those at 13 to 17 weeks of gestation, and also increase in women who are delivered preterm. Theoretically, oxytocin antagonists might provide effective tocolysis, because systemic side effects would be minimal because of organ specificity.

Several studies describe the effects of oxytocin antagonists in vitro. One investigated the ability of 1-deamino-2-D-Tyr(0-ethyl)$^4$-Thr$^8$Orn-oxytocin to inhibit binding of oxytocin in decidual and myometrial membranes of the rat, guinea pig, and human. Decidua and myometrium of all three species bound tritium-labeled oxytocin with high affinity, and 1-deamino-2-D-Tyr(0-ethyl)$^4$-Thr$^8$-Orn-oxytocin completely displaced labeled oxytocin from binding sites in all tissues. Another examined a synthetic oxytocin antagonist [β-mercapto-β,β-cyclopentamethylene propionic acid, D-Trp$^2$-Ile$^4$-Arg$^8$]-vasopressin. This compound inhibited oxytocin-induced contractions in the nonpregnant rat uterus, in vitro and in vivo. It also inhibited milk letdown in the lactating rate, disrupted labor in the rat, and inhibited the in vitro response to oxytocin of myometrium obtained from women. Four oxytocin analogs, 1-deamino-2-D-Tyr[0-ethyl]$^4$-Val$^8$-Orn-vasotocin, 1-deamino-2-D-Tyr[0-ethyl]$^4$-Thr$^8$-Orn-vasotocin, 1-deamino-2-L-Tyr[0-ethyl]$^4$-Thr$^8$-Orn-vasotocin, and 1-deamino-2-D-Trp$^4$-Thr$^8$-D-Arg-vasotocin, displaced oxytocin and arginine vasopressin in myometrial membrane preparations from pregnant women at term.

Two reports describe the use of oxytocin antagonists in women in pre-term labor. The first used 1-deamino-2-D-Tyr[0-ethyl]$^4$-Thr$^8$-Orn-oxytocin in 13 patients. Uterine activity was inhibited in all patients. However, 10 patients received subsequent therapy with β-sympathomimetics, and three (23%) were delivered pre-term. A second study used intravenous infusions of 1-deamino-2-D-Tyr[0-ethyl]$^4$-Thr$^8$-Orn-oxytocin in 12 patients in premature labor. All patients were initially placed at bed rest for 2 hours and were treated if contractions persisted. Complete tocolysis was noted in six patients, partial tocolysis in three patients, and no tocolytic effect in three patients. The three patients in whom there was no effect were less than 28 weeks pregnant and were subsequently treated with ritodrine. Ultimately, 7 of 12 patients were delivered preterm. No maternal side effects, fetal heart rate abnormalities, or complications with breast-feeding were atttibutable to treatment. No comments were made regarding neonatal morbidity or mortality.

Prostaglandin Inhibitors

Local prostaglandin production probably plays a role in cervical ripening and may modulate uterine activity in labor. Many birthing centers use prostaglandin $E_2$ gel for cervical ripening. Both prostaglandin $E_2$ and prostaglandin $F_{2\alpha}$ are used for induction of labor in the second trimester of pregnancy.

Prostaglandins exhibit uterine effects in two ways. First, they enhance production of myometrial gap junctions. Second, prostaglandin $F_{2\alpha}$ stimulates the influx of intracellular calcium and the release of calcium from the sarcoplasmic reticulum. This increase in intracellular calcium leads to activation of myosin light chain kinase and subsequent muscle contraction. Elevated levels of prostaglandins in plasma and amniotic fluid have been demonstrated during normal human parturition. Levels are low or absent in serum and amniotic fluid of patients not in labor at all states of pregnancy. Prostaglandin metabolites are significantly reduced in patients treated with indomethacin. They are also significantly higher in patients who are delivered pre-term than in patients with prolonged gestation.[32]

All prostaglandin synthetase inhibitors act by inhibiting the enzyme cyclooxygenase. This enzyme is found throughout the body and in high concentrations in the myometrium. Cyclooxygenase converts arachidonic acid into the first prostaglandin intermediate prostaglandin $G_2$. All subsequent prostaglandins are derived from this initial step. Aspirin causes irreversible inhibition of this enzyme by acetylation. Indomethacin competes with arachidonic acid for cyclooxygenase. Therefore it does not disrupt the enzyme. When indomethacin levels decrease, enzyme activity resumes. These drugs have anti-inflammatory, antipyretic, and analgesic properties. They also suppress formation of prostacyclin and thromboxane $A_2$. Indomethacin, naproxen, and fenoprofen are more effective than aspirin as inhibitors of prostaglandin synthesis.

Nonsteroidal anti-inflammatory drugs differ in chemical structures, mechanisms of action, and side effects. Therefore one cannot assume that an effect observed with a particular agent will be found with another. These drugs effectively inhibit contractility of the pregnant and nonpregnant myometrium. They are more effective than the $\beta$-sympathomimetics. There has been no report of suppression of uterine contractions with $\beta$-adrenergic agonists after failed treatment with a prostaglandin inhibitor; but several studies show the opposite.

Interest in prostaglandin inhibitors begin in 1973. A retrospective study showed that patients taking high-dose salicylates during pregnancy had significant increases in mean length of gestation, frequency of postmaturity, and mean duration of spontaneous labor. In a second study patients taking long-term salicylates during pregnancy had a higher incidence of gestation extending beyond 42 weeks. Another study demonstrated that administration of oral aspirin or indomethacin prolonged the injection-to-abortion interval in patients undergoing midtrimester abortion with hypenonic saline solution. Finally, low doses of aspirin prolonged the injection-to-abortion interval in nulliparous patients undergoing midtrimester abortion with hyperosmolar urea and continuous oxytocin infusion.

The first report of the use of these drugs to stop premature labor was published in 1974. Treatment of 50 patients in premature labor with indomethacin delayed delivery >7 days in 40 patients (80%). Numerous subsequent studies have attempted to evaluate the efficacy of prostaglandin inhibitors in treating premature labor.

Prostaglandin inhibitors are not associated with serious adverse effects on mother or fetus. There were no major problems in the newborns of 297 women treated with indomethacin.

These compounds differ in chemical structures, mechanisms of action, and side effects. Common adverse effects include nausea, vomiting, diarrhea, heartburn, headache, dizziness, and allergic rash. More serious toxicity is manifested by thrombocytopenia, peptic ulceration, bleeding, and serious allergic reactions. In addition, prostaglandin inhibitors may mask signs of infection.

The main concern with this class of drugs is the potential for adverse effects on the fetus, particularly premature closure of the ductus arteriosus. Indomethacin is used to treat persistent patency of the ductus arteriosus in the pre-term neonate. Clinical response in the pre-term neonate is variable and not related to serum indomethacin concentration. Most studies demonstrate resistance of the ductus to closure at earlier gestational ages. Prostaglandin inhibitors cause constriction of the fetal ductus arteriosus in utero. The constriction is transient and usually abates after cessation of the drug. However, prolonged exposure to indomethacin may lead to persistent pulmonary hypertension and tricuspid insufficiency in the neonate.

Other fetal complications include impaired renal function with resultant oligohydramnios. Indomethacin has also been used to treat polyhydramnios and normalize amniotic fluid volume. This drug may be especially useful for treating preterm labor in patients with polyhydramnios. There is little evidence that indomethacin causes permanent renal impairment in the neonate; one case report documented a monozygotic twin gestation with polyhydramnios in which the mother was treated with indomethacin and the fetus had renal digenesis.

Calcium Channel Blockers

Calcium channel blockers inhibit spontaneous myometrial contractions and suppress prostaglandin- and oxytocin-induced uterine contractions in vitro and in vivo. The main site of action is the cell membrane, where influx of extracellular calcium through voltage-dependent calcium channels is inhibited. Verapamil, but not nifedipine, impairs atrioventricular conduction and can cause cardiac dysfunction.

The use of verapamil for treating pre-term labor was first reported in 1972. Effectiveness of treatment could not be shown because dosage was limited after cardiovascular side effects. The first study using nifedipine to treat premature labor was reported in 1977. Ten patients in pre-term labor were treated. Labor stopped in all patients. In a similar study of 20 patients, 15 had delivery delayed for >3 days. A subsequent study documented delay of delivery in eight patients with chronic hypertension, until after 38 weeks of gestation. Mean gestational age at entry was 30 weeks. The patients became normotensive during therapy.

Delivery was delayed for >48 hours in 9 of 13 patients treated with nifedipine. Ghirardini (1991) reported successful treatment of eight women in premature labor. All were delivered after 38 weeks' gestation. In another study uterine contractions were inhibited in 16 of 22 patients in pre-term labor treated with nifedipine; 13 experienced undesirable side effects.

Two prospective, randomized studies compared nifedipine with ritodrine. The first randomly allocated 20 women to ritodrine, 20 women to nifedipine, and 20 women to no treatment. Success was defined as delay of delivery for 48 hours. Seventy-five percent success was achieved in the nifedipine group, compared with 45% in the ritodrine group and 29% in the placebo group. This study has been criticized for possible selection bias, poor reporting of side effects, and the fact that 25% of the nifedipine group were subsequently treated with ritodrine.

A recent study randomized 33 patients to ritodrine and 33 patients to nifedipine. Delivery was postponed for 48 hours in 84% of the nifedipine group and 72% of the ritodrine group. Delivery was delayed for 7 days in 70% of women treated with nifedipine and 52% of those treated with ritodrine. Maternal side effects were more common in patients treated with ritodrine (p<0.01). Fetal and neonatal outcomes were similar in the two groups.

Calcium channel blockers produce vasodilation and decrease peripheral vascular resistance. Transient facial flushing is the most common side effect, but then can also cause nausea and headache. Maternal side effects appear to be less than with the β-sympathomimetics. Nifedipine potentiates the toxicity of magnesium sulfate by causing neuromuscular blockade. It also causes maternal hepatotoxicity. Although no serious fetal or neonatal side effects have been reported, these drugs may diminish uteroplacental blood flow.

In addition to the individual treatments discussed above, tocolytic treatments of the inventions can also involve combinations of the individual treatments listed above or other treatments not listed here.

Intensity of a given tocolytic treatment will generally be correlated to the concentration of the drug being administered, the duration of administration, or the frequency of administration. However, a change in intensity can also refer to a change in the type of treatment from one generally considered less effective but with fewer side effects to one which is more potent but which has potentially greater side effects.

With regard to the side effects of the various treatments above, it should be recognized that this specification is not intended to recommend any particular treatment. That decision should be made by the attending physician, who will generally make a decision based on both the potency of the drug being administered as a tocolytic and on the potential side effects using both the results of estriol monitoring and other clinical signs.

By detecting the probable onset of premature labor and monitoring tocolytic treatment as described herein, a physician will be able to use existing techniques for delaying labor to avoid premature delivery and the resulting high risk of infant death.

EXAMPLE

Saliva samples were obtained from four patients at weekly intervals during pregnancy and analyzed by celite chromatography. All patients were considered at risk for premature labor. Three patients had previously given birth at less than 35 weeks of gestation. The remaining patient was at risk because she had a uterine anomaly. The attending physician did not correlate estriol levels to clinical signs in this study (i.e., it was a blind study), since the purpose of this evaluation was to determine whether tocolytic treatments would modify estriol levels after administration of a tocolytic and to determine whether estriol levels after tocolytic treatment were indicative of likely future events, such as resumption of uterine contractions and/or pre-term delivery. The results are summarized in Table I below (uc:uterine contractions; cd: cervical dilation (cm); Toc: tocolytic treatment; LMP: last menstrual period).

TABLE I

| Days Gestation (as measured from LMP) | Patient 1 (201) estriol (nmol/l) | Comment | Patient 2 (263) estriol (nmol/l) | Comment | Patient 3 (226) estriol (nmol/l) | Comment | Patient 4 (214) estriol (nmol/l) | Comment |
|---|---|---|---|---|---|---|---|---|
| 140 | | | 0.49 | no uc no cd | | | | |
| 147 | | | 1.3 | | | | | |
| 161 | | | 1.6 | | | | | |
| 168 | | | 1.8 | cramps no cd | | | | |
| 169 | 1.2 | uc | | | | | | |
| 174 | | | 2.7 | | | | | |
| 176 | 1.3 | | | | | | | |
| 181 | | | 1.1 | uc cd = 0.5 | | | | |
| 183 | (1.4) | no uc no cd | | | | | | |
| 189 | | | 4.7 | no uc Toc | | | | |
| 190 | 3.0 | | | | | | | |
| 196 | | | 3.6 | | | | | |
| 197 | | | | | | | 2.4 | no uc no cd |
| 198 | 3.9 | uc no cd | | | | | | |
| 202 | | | 6.2 | uc Toc cd = 0.5 cm | | | | |
| 205 | | | | | | | 2.9 | no uc no cd |
| 209 | | Toc | 3.4 | uc cd = 0.5 Toc | | | | |
| 211 | 1.4 | uc cd = 2 | | | | | | |
| 212 | | | | | | | 3.8 | |
| 216 | | | 4.9 | uc cd = 0.5 | | | | |

TABLE I-continued

| Days Gestation (as measured from LMP) | Patient 1 (201) estriol (nmol/l) | Comment | Patient 2 (263) estriol (nmol/l) | Comment | Patient 3 (226) estriol (nmol/l) | Comment | Patient 4 (214) estriol (nmol/l) | Comment |
|---|---|---|---|---|---|---|---|---|
| 217 | 0.6 | Toc stopped | | Toc | | | | |
| 219 | | | | | | | 3.7 | |
| 223 | | | 4.5 | uc Toc cd = 0.5 | | | | |
| 226 | 1.2 | uc cd = 2 | | | | | | |
| 227 | | | | | | | | Toc |
| 230 | | | 3.4 | uc cd = 2 Toc | | | | |
| 232 | 0.6 | no uc cd = 2 | | | | | | |
| 233 | | | | | | | 1.4 | uc |
| 235 | | | | Toc stopped | | | | |
| 236 | | | | | 5.4 | uc cd = 1 | | |
| 240 | | C-section | | | | Toc | | |
| 243 | | | 5.2 | uc cd = 2 no Toc | | | | |
| 244 | | | 7.4 | no Toc | | | | |
| 245 | | | | | | | | Toc stopped |
| 247 | | | | no Toc delivery | | | | |
| 249 | | | | | | | 7.8 | uc cd = 1.5 no Toc |
| 252 | | | | | | uc cd = 2 no Toc | | |
| 253 | | | | | 8.5 | | | |
| 254 | | | | | | | 9.7 | uc cd = 3.5 |
| 255 | | | | | | delivery | | delivery |

Patient 1 [Patient 201] showed an increase in estriol levels prior to traditional indications of imminent pre-term labor (discernible cervical change in dilation and effacement, presence of strong, regular uterine contractions, spontaneous rupture of membranes) at 28 2/7 weeks gestation (day 198). (Gestational dating was determined from the Last Menstrual Period (LMP)). Tocolytics were administered at 29 6/7 weeks gestation (day 209) for discernible cervical change (to 2 cm dilation) and contractions. Magnesium sulfate was administered intravenously using a dosage of 2 gm STAT, then 1 gm hourly for 48 hours until 30-1/7 weeks gestation when it was terminated. Indomethacin, a prostoglandin inhibitor, was administered at a dose of 25mg–50mg depending on symptoms, every 4 hours by mouth until 31 weeks gestation when it was terminated on Day 211. After tocolytic treatment, the estriol concentration decreased to substantially normal values and there was no further cervical change, and the pregnancy was maintained for three weeks until delivery by cesarean section for breech presentation at a gestational age of 34-2/7 weeks (Day 240).

With Patient 2 [Patient 263], estriol levels again mirrored the onset of pre-term labor. After the appearance of clinical symptoms such as backache, pelvic pressure and uterine contractions, tocolytic treatment was initiated at 27 weeks (day 189). Specifically, terbutaline was administered to the patient by mouth at a dose of 5mg at 6-hour intervals. After three weeks treatment, the dosage of terbutaline was increased to 5 mg every 3 hours. At the beginning of the 6th week of tocolytic treatment (Day 235), MgSO$_4$, at a dosage of 3 gm/hr administered intravenously, was substituted for terbutaline for four days (beginning Day 235 through Day 239). On Day 239, MgSO$_4$ administration was discontinued. Salivary estriol levels, which were measured weekly, dropped by day 209 but rose again at 243 days, to 5.181 nanomoles per liter (nmol/l). Since the physician was not correlating the estriol level with the tocolytic treatment, the tocolytic treatment was discontinued at Day 235. A pre-term delivery by cesarean section occurred at 35-2/7 weeks (Day 247) gestation following probable spontaneous rupture of membranes 24 hours before.

Patient 3 [Patient 226] had an elevated estriol level on day 236 and exhibited symptoms of pre-term labor, namely uterine contractions and 1 cm cervical dilation, but was not on tocolytics. After exhibiting continued contractions with cervical change, the patient was administered with a single dose of 0.25 mg terbutaline by subcutaneous injection at gestation weeks 34-2/7 Coy LMP, day 240). At 34-6/7 weeks (day 244), she had an increase in salivary estriol value, and at 36-1/7 weeks (Day 252; patient's physician was not monitoring estriol), the salivary estriol levels increased even further to 8.506 nmol/l. Two days later she delivered at 36-3/7 weeks.

Patient 4 [Patient 214] had been seen by her physician at days 197, 205, 212 and 219 with no symptoms of pre-term labor and borderline surge in estriol on days 212 and 219. At 32-3/7 weeks' gestation (Day 227), she was diagnosed as having pre-term labor and terbutaline was administered by mouth every 3-4 hours at a dose of 5mg until 35 weeks gestation (Day 245). Her estriol levels, measured weekly, dropped during treatment to 1.792 nmol/l at 233 days but after termination of treatment, at day 249 (35-4/7 weeks) her estriol levels were high again at 7.77 nmol/l. The physician was not monitoring estriol levels, no tocolytics were administered, and the patient had a spontaneous vaginal premature delivery at 36-3/7 weeks (Day 255).

The invention now being fully described, it will be apparent to one of ordinary skill in the art that many changes and modifications can be made thereto without departing from the spirit or scope of the appended claims.

All publications and patent applications mentioned in this specification are herein incorporated by reference to the same extent as if each individual publication or patent application was specifically and individually indicated to be incorporated by reference.

What is claimed is:

1. A method of monitoring tocolytic therapy, which comprises:
   measuring a first concentration of estriol in a body fluid of a pregnant patient undergoing or diagnosed as a candidate for undergoing treatment with a tocolytic agent;
   correlating said first concentration with a predetermined standard estriol value; and based on said first concentration and its correlation to said predetermined standard estriol value, either initiating, continuing, discontinuing, or modifying said tocolytic treatment.

2. The method of claim 1, wherein said correlating comprises comparing said concentration with a standard value selected from the group consisting of
   (1) a predetermined range of estriol concentrations for said body fluid in normal pregnant humans or
   (2) a previously measured estriol concentration of said body fluid of said pregnant human.

3. The method of claim 1, wherein a higher concentration of estriol relative to said standard value is utilized as an indication of initiation, continuation, or increase of intensity of said tocolytic treatment.

4. The method of claim 1, wherein a concentration of estriol less than or equivalent to said standard value is utilized as an indication of cessation or decrease of said tocolytic treatment.

5. The method of claim 1, wherein said first estriol concentration is higher than said standard and said tocolytic treatment is initiated, continued, or increased and said estriol concentration is measured over time until said concentration reaches a predetermined second estriol concentration lower than said standard.

6. The method of claim 1, wherein said determining is carried out on a sample of a body fluid of said patient.

7. The method of claim 6, wherein said body fluid is saliva, plasma, serum, urine, cervical or vaginal secretion, or sweat.

8. The method of claim 6, wherein said body fluid is saliva and said concentration is considered to be an indication of initiation, continuation, or increase of said tocolytic treatment when said concentration exceeds 5 nM and an indication of cessation or decrease of said tocolytic treatment when said concentration is less than 3 nM.

9. The method of claim 1, wherein when said method is carded out prior to tocolytic treatment and said concentration exceeds a previously measured estriol concentration made in said body fluid in said pregnant human within one week by 50%, tocolytic treatment is initiated.

10. The method of claim 1, wherein said method is carded out prior to tocolytic treatment and said concentration is at least as high as the 95th percentile concentration for said body fluid for a normal pregnancy at 40 weeks and said concentration is measured at 30 weeks or earlier, tocolytic treatment is initiated.

11. The method of claim 1, wherein said method detects only unconjugated estriol.

12. The method of claim 1, wherein said method is carded out after initiating tocolytic treatment and tocolytic treatment is halted when said concentration reaches a measurement value no higher than 1 standard deviation above said standard value.

13. The method of claim 1, wherein said method is carried out after initiating tocolytic treatment and tocolytic treatment is halted when said concentration reaches a measurement value no higher than 1 standard deviation below said standard value.

* * * * *